United States Patent [19]

Mittelmeier et al.

[11] 4,355,429
[45] Oct. 26, 1982

[54] SLIDE PROSTHESIS FOR THE KNEE JOINT

[75] Inventors: Heinz Mittelmeier, Blieskastel, Fed. Rep. of Germany; Heinz Moser, Selzach; Beat Leu, Ipsach, both of Switzerland

[73] Assignee: Osteo AG, Selzach, Switzerland

[21] Appl. No.: 114,335

[22] Filed: Jan. 23, 1980

[30] Foreign Application Priority Data

Jan. 26, 1979 [EP] European Pat. Off. ........ 79810010.3

[51] Int. Cl.$^3$ .............................................. A61F 1/03
[52] U.S. Cl. ................... 3/1.911; 128/92 C
[58] Field of Search ...................... 3/1.9, 1.91, 1.911, 3/1.912, 1.913; 128/92 C, 92 CA

[56] References Cited

U.S. PATENT DOCUMENTS

| | | | |
|---|---|---|---|
| 2,910,978 | 11/1959 | Urist | 3/1.912 X |
| 3,053,251 | 9/1962 | Black et al. | 128/92 CA |
| 3,774,244 | 11/1973 | Walker | 3/1.911 |
| 3,808,606 | 5/1974 | Tronzo | 128/92 CA X |
| 3,893,196 | 7/1975 | Hochman | 3/1.91 |
| 3,953,899 | 5/1976 | Charnley | 3/1.911 |
| 3,958,278 | 5/1976 | Lee et al. | 3/1.911 |
| 3,977,026 | 8/1976 | Battavlt | 3/1.91 |
| 3,987,499 | 10/1976 | Scharbach et al. | 3/1.9 X |
| 4,000,525 | 1/1977 | Klawitter et al. | 3/1.91 X |
| 4,055,862 | 11/1977 | Farling | 3/1.91 |
| 4,064,568 | 12/1977 | Grundei et al. | 3/1.911 |
| 4,094,017 | 6/1978 | Matthews et al. | 3/1.911 |
| 4,146,936 | 4/1979 | Aoyagi et al. | 3/1.91 |

FOREIGN PATENT DOCUMENTS

| | | | |
|---|---|---|---|
| 2603456 | 8/1977 | Fed. Rep. of Germany | 3/1.9 |
| 2636644 | 2/1978 | Fed. Rep. of Germany | 3/1.912 |
| 2216981 | 9/1974 | France . | |
| 2269928 | 12/1975 | France . | |
| 2339388 | 8/1977 | France . | |
| 2350825 | 12/1977 | France . | |

Primary Examiner—Clifford D. Crowder
Attorney, Agent, or Firm—Wender, Murase & White

[57] ABSTRACT

A slide prosthesis for the knee joint is provided to be secured free of cement, the tibia members, the femur members and the surface replacement for the knee cap having anchoring pins which are provided with a saw tooth-like or bone screw-shaped profile. The tibia and knee cap members are preferably made of carbon fibre-reinforced plastics material and the femur members of aluminium oxide ceramic material. In order to assist growth of the bone to the prosthesis members, the members are coated at the corresponding points with bioactive particles, such as apatite-containing glasses, apatite particles or dealbumined bone material.

9 Claims, 6 Drawing Figures

SLIDE PROSTHESIS FOR THE KNEE JOINT

BACKGROUND OF THE INVENTION

In the treatment of damaged knee joints, hinged prostheses of metal were originally used. These parts were anchored with the use of long anchoring pins, originally without cement, in the thigh bone and in the shin bone. Due to loosening, such prostheses were then recommended, and more particularly, for additional security, to be secured using bone cement. However, in these cases, aseptic loosening occurred in many cases on the cement layer; in addition, there were doubts over a long period with regard to the use of bone cement, particularly in the case of comparatively young people. The high degree of wear on the metal in the region of the hinge axes also resulted in damage to the tissue from the metal powder with an increased yield of metal ions. Improvements by utilising polyethylene slide bearings in the region of the axes or the surface of the joint were able to solve the problem only to an unsatisfactory extent. In particular, the considerable condylene resection necessary for this joint replacement and excavation of the marrow area appeared particularly unfavourable in the event of failure, since with the removal of these prostheses and consequent arthrodesis, i.e., a stiffening of the joint, a considerable shortening of the leg had to be accepted.

Therefore, to an increasing extent, the replacement of the surface of the knee joint in the form of so-called slide prosthesis has become popular, for which purpose only a slight surface bone resection is necessary, so that in the event of failure, the possibility of return to a hinged prosthesis or a reinforcement of the joint is possible without any considerable shortening resulting therefrom.

Conventional slide prostheses of various manufacture exist in the femur portion, particularly of metal slides adapted to the thigh bone and corresponding shin bone head surfaces of polyethylene which can be used for one of the two halves of the joint separately, or for both halves independently of each other, or in combination with each other. In the combination of the parts of the femur, a slide bearing for the knee cap is also desired. A polyethylene surface replacement for the sliding surface of the knee cap may also be provided.

Such forms of slide prostheses to be anchored with bone cement, however, have various disadvantages, such as deformation of the plastics material, relatively high wear of the plastics material and the already mentioned risk of the crumbling of the relatively thin cement layer and, consequently, aseptic loosening of the prostheses and, in the case of comparatively young people, in particular also the above-mentioned doubts on the durability of the bone cement. More particularly, frequent loosening of the tibia components was noticed.

SUMMARY OF THE INVENTION

It is consequently an object of the present invention to provide a slide prosthesis for the knee joint, which in particular can also be secured in position over a long period without bone cement and which has on the joint surfaces much less wear and a better frictional co-efficient than the above-mentioned conventional slide prostheses.

According to the present invention there is provided a slide prosthesis for the knee joint, in which the prosthesis members secured without cement, for the femur, the tibia and the patella have anchoring pins with saw toothlike or bone screw-shaped profiles.

In preferred embodiments, one part of the joint is manufactured of carbon fibre-reinforced plastics material and the other prepared from aluminium oxide ceramic material, or both parts are prepared from aluminium oxide ceramic material. For the purpose of better adhesion of the bone to the parts of the prosthesis, said parts are coated with apatite or bioglass on the portions thereof coming into contact with the bones.

BRIEF DESCRIPTION OF THE DRAWINGS

The present invention will be further illustrated by way of example with reference to the accompanying drawings, in which.

DESCRIPTION OF PREFERRED EMBODIMENTS

Figure 1:
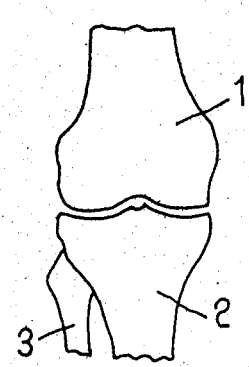
FIG. 1 is a schematic front view of a knee joint.

FIG. 1 schematically illustrates the bone components of the knee joint, viz: the femur 1 or thigh bone, the tibia 2 or shin bone, and the fibula 3, or splint-bone.

Figure 2:
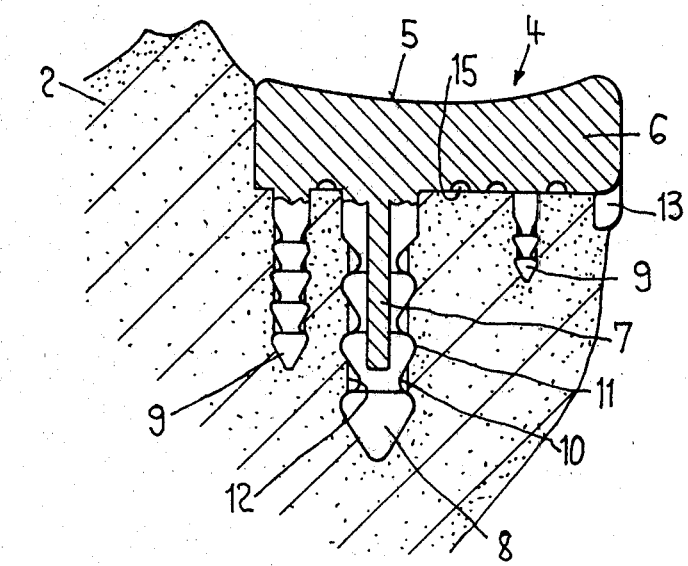
FIG. 2 is a sectional view, on an enlarged scale, of a preferred embodiment of a prosthesis member according to the present invention attached to a shin bone.
Figure 3:
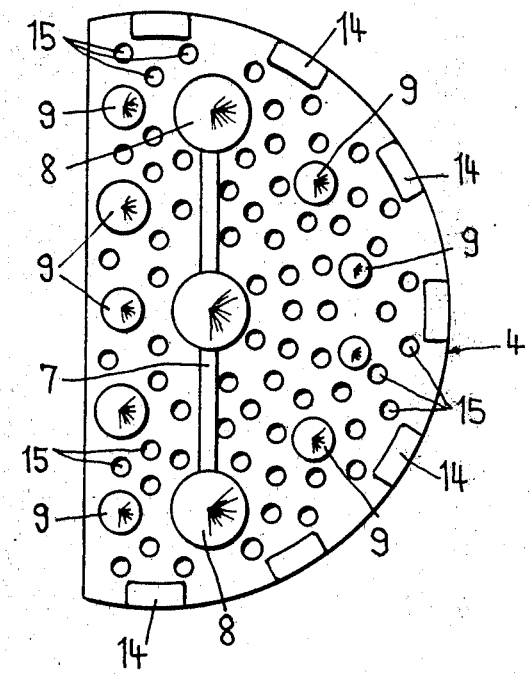
FIG. 3 is an underneath plan view of the prosthesis member shown in FIG. 2.

FIG. 2 shows in section, a preferred embodiment of a prosthesis member 4 for the shin bone 2, referred to as the tibia hereinafter. The surface 5 of the joint is slightly concave, corresponding to the natural joint surface of the shin bone, whilst the thickness of the plate 6 may be varied for the compensation of condylene effects. In the present embodiment, the tibia portion has an anchoring flange 7 extending in the longitudinal axis of the prosthesis member, said flange being provided with three relatively thick anchoring pins 8 (FIG. 3). The tibia portion is also provided along its edge with a number of anchoring pins 9 of different diameter. All the anchoring pins 8 and 9 are provided, in the present embodiment, with a saw tooth-like profile having constrictions 10 and protuberances 11. Instead of this saw tooth-like profile, the anchoring pins may have a bone screw profile or any other suitable thread may be used. From FIG. 2, it is apparent that the diameter of the bores 12 is somewhat greater than the diameter of the constrictions 10 and somewhat smaller than the diameter of the protuberances 11 whereby an excellent anchorage is achieved when these pins are knocked in and, moreover, the bone can grow into the constrictions 10. For the purpose of strengthening the anchorage, the lower edge of the plate 6 is provided with a flange 13 overlapping the lateral condylene edge, said flange 13 comprising either a continuous member or, as shown in FIG. 3 a plurality of individual teeth 14. By this means, better protection from slipping is effected and support on the natural condylene edge is provided. The surface of the plate 6 facing the bone is provided, in order to increase the anchorage, with cavities 15 about the size of a pin head, which are arranged in a honeycomb-like structure. In the case of total knee arthrosis, it is proposed that both parts of the tibia 2 may be connected by provision of a bridge to form a unit in the front portion. This renders possible a surface replacement in the median and lateral condylene area as well as on the slide bearing of the patella.

As materials for the production of these parts of the tibia, metals or metal alloys, for example, titanium, chromium-cobalt-, chromium-cobalt-molybdenum alloys or aluminium oxide ceramics may be used. However, the use of carbon fibre-reinforced synthetic plastics material, for example, polyethylene, appears very advantageous, since due to this fibre reinforcement, the synthetic material becomes stronger in the first instance so that plastic deformations can be avoided. In addition, friction can also be reduced thereby. In particular, however, there is also an increase in the modulus of elasticity which means that the elastic deformation is also less, so that loads do not have such a strong local effect on the bone bearing. The carbon fibres should preferably be distributed in such manner that the fewest possible fibres are in the layer near the bone in order to achieve a modulus of elasticity which is substantially equal to that of the bone, in order to avoid relative movements between the part of the prosthesis member and the bone. At the same time, short staple fibres of a few millimeters in length may be mixed with a pulverised synthetic material, the prosthesis member being prepared by subsequent thermo-sintering with impression into the mould. However, it is also possible to liquefy a mixture of thermo-plastic synthetic powder and corresponding carbon fibres and to pour same into the prosthesis mould. In the case of construction of parts of the prosthesis which are particularly stressed, either the carbon fibres may be arranged in separate directions or long fibre strips or fibre fabrics may be used.

Figure 4:
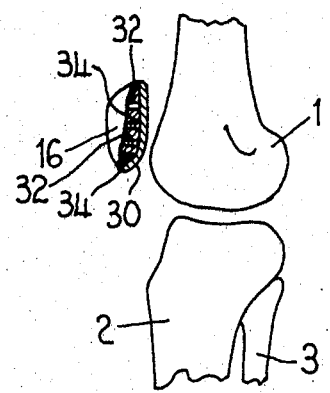
FIG. 4 is a schematic side view of a knee joint.
Figure 6:
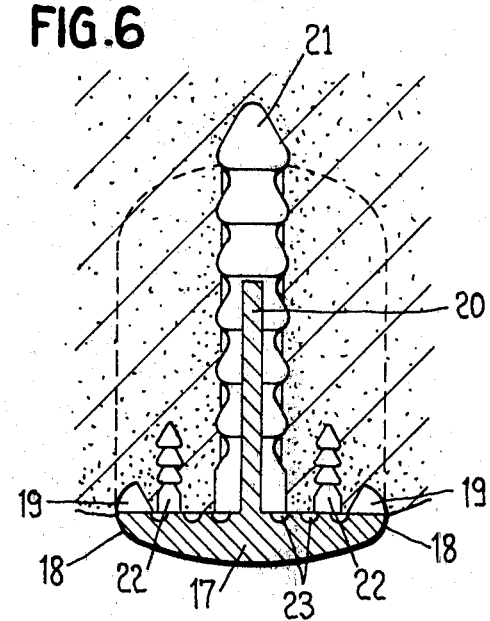
FIG. 6 is a cross-sectional view of the prosthesis member of FIG. 5.

FIG. 4 is a schematic side view of the knee joint, and again part of the femur 1, the tibia 2 and the fibula 3 as well as the patella or knee cap 16 are shown.

Figure 5:
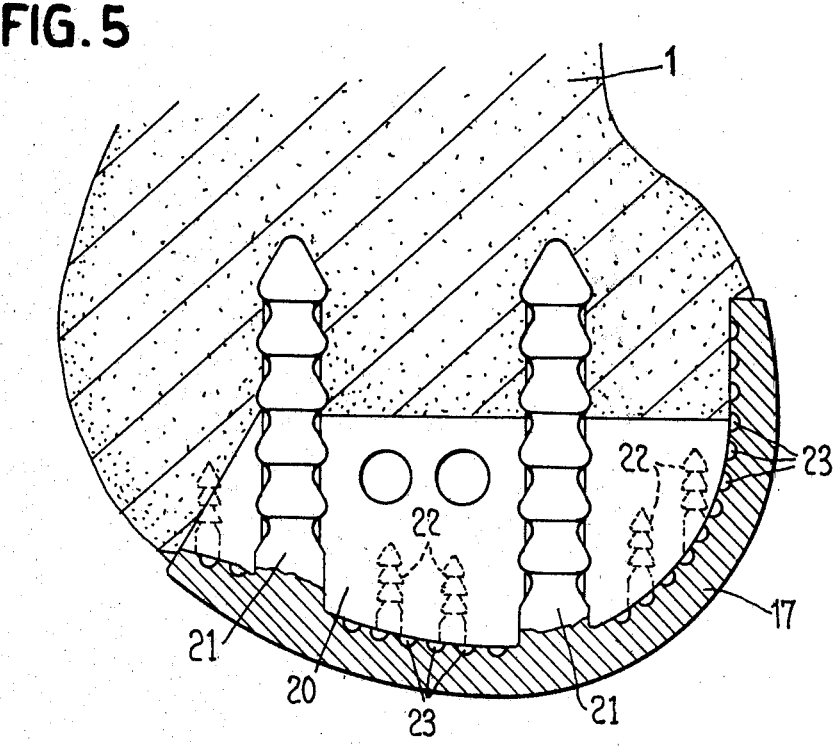
FIG. 5 is a longitudinal section, on an enlarged scale, of a second embodiment of a prosthesis member according to the present invention attached to a thigh bone.

FIG. 5 shows in section the prosthesis member for the femur 1, a femur member 17 in the form of a runner of a sledge which is adapted to the shape of a convex condylene. The edges 18 are somewhat curved and bevelled in the direction of the bone and are provided on the ends with teeth 19 which render possible improved interlocking. Similarly to the tibia portion 2, the femur portion also has an anchoring flange 20 which is reinforced, for example, by two main anchoring pins 21, as well as having other smaller anchoring pins 22 of different diameters, the profile of the anchoring pins being the same as that of the anchoring pins of the tibia portion. In addition, the side of the prosthesis member facing the bone has cavities 23 which are used for improved anchorage. Corresponding to the tibia portion, it is also proposed, in the case of the femur portion, that the slides for the median and lateral femur condyls should be connected in the front region of the joint so that a replacement of the knee cap slide bearing is also provided.

As in the case of the tibia, both metals tolerated by the body and metal alloys or aluminium oxide ceramics or carbon fibre-reinforced synthetic materials may be considered as material for the femur portions, various pairings of the femur and tibia portions being possible, for example, the femur portions may be of metal or aluminium oxide ceramic and the tibia portions of carbon fibre-reinforced plastics material or, conversely, the tibia portions may be of metal or aluminium oxide ceramic and the femur portions of carbon fibre-reinforced plastics material or all the portions of aluminium oxide ceramic or all the portions of carbon fibre-reinforced plastics material.

The surface replacement for the knee cap is effected in a similar manner, as by the use of a prosthesis 30 wherein the surface of the joints being adapted to the surface of the patella slide bearing of the femur condylus and the side facing the bone being provided in a similar manner as described above with at least two main achoring pins 32 and several secondary anchoring pins 34, all with saw-tooth or bone-screw profile, and honeycomb-like cavities for the growing-in of the bone.

A further improvement for the growing of the bone into the prosthesis may be achieved by biological surface activation, by the incorporation of non-resorbable bio-active particles, wherein apatite-containing glasses, so-called bioglass, apatite particles and hetero-homo- and auto-plastic dealbumined bone particles are intended. In the case of prosthesis members of carbon fibre-reinforced plastics material, these particles should be super-equatorially enclosed in the prosthesis surface in question, whilst the intermediate plastics material may serve in practice as an expansion joint, whereby crumbling or splitting of the bio-active material is avoided by elastic or plastic deformation, in contrast to previously proposed coherent coatings.

The incorporation of the bio-active particles in the surface of the prosthesis can be achieved for example if they applied, originally with an adhesive which is soluble in water, as much as possible to the corresponding places of the prosthesis mould by shaking thereon and then during the casting of the heated liquids plastics material, are melted or pressed into the surface during the pouring of the heated, liquid plastics material with the carbon fibres or by heat moulding of finely powdered plastics material.

The coating or incorporation of the bio-active particles into metal or aluminium oxide ceramic material may be effected in principle in a similar manner, i.e. by the pouring of metal onto a similarly coated mould or by pouring the aluminium oxide ceramic paste onto the mould and subsequent burning in. In any case, it is an advantage to achieve a non-incoherent coating. In the case of aluminium oxide ceramic particles of apatite-containing glasses are preferably used.

The incorporation of these bio-active particles into the surfaces of the prostheses resting on the bones contributes to further roughening, and thus enlargement of the surface, and hence to reducing the specific pressure. In particular, this renders possible—in conjunction with the fixed, primary, mechanical anchorage—direct growing of the bone tissue without an intermediate layer of bonding tissue and a physio-chemical combination of the prosthesis in the bone tissue in the sense of a microscopic spot welding operation. At the same time, the chemical effect of the non-bio-active prosthesis material on the bone tissue and hence the danger of foreign body reaction is reduced.

The operating technique for the insertion of prosthesis members proceeds from the conventional operating technique for such parts. After exposing and preparing the corresponding portions of bone, a stencil corresponding to the prosthesis member to be used is applied and the slit necessary for the anchoring flanges is cut in accordance with the stencil, and the bores for the anchoring pins drilled. In the event of two anchoring flanges extending perpendicularly to each other being applied, a corresponding stencil must be used. In certain cases it may be necessary or advantageous to fix the stencil temporarily by means of a spongiosa screw in order the prevent displacement during the drilling of the holes. Subsequently, the prosthesis member is applied and knocked in by means of a special instrument, a curved instrument having to be used for example, for knocking in the tibia members, since the thigh bone would impede a straight instrument.

We claim:

1. A slide prosthesis for cementless attachment to a knee joint, comprising:
    a joint member having a joint surface and an opposite mounting surface;
    at least two primary securing pins extending from the mounting surface of said joint member to attach the prosthesis to the joints;
    a plurality of secondary securing pins extending from the mounting surface of said joint member adjacent the periphery thereof to supplement the attachment of the prosthesis to the joint, said secondary securing pins being smaller than and parallel to said primary securing pins;
    each of said primary and secondary securing pins having a ridged profiled with interstices for admission of bone growth so as to preclude unintentional dislodgement of the prosthesis from the knee joint; and
    a support plate extending from the mounting surface of said joint member and connected to and extending between said primary securing pins.

2. A slide prosthesis as recited in claim 1, wherein said ridged profile of said primary and secondary securing pins is saw-tooth like.

3. A slide prosthesis as recited in claim 1, wherein said ridged profile of said primary and secondary securing pins is bone-screw shaped.

4. A slide prosthesis as recited in claim 1, further including a flange extending from the peripheral edge of said mounting surface of said joint member in the direction of said securing pins.

5. A slide prothesis as recited in claim 4, wherein said flange is segmented to form a plurality of individual teeth.

6. A slide prosthesis as recited in claim 1, wherein said mounting surface defines a plurality of cavities arranged in a honeycomb-like pattern.

7. A slide prosthesis as recited in claim 1, wherein said joint member and said primary and secondary securing pins comprise a unitary structure.

8. A slide prosthesis as recited in claim 1, wherein at least said joint member is made of a carbon fiber-reinforced plastic material.

9. A slide prosthesis as recited in claim 1, wherein at least said joint member is made of aluminium oxide ceramic material.

* * * * *